(12) United States Patent
Steiner et al.

(10) Patent No.: US 8,114,077 B2
(45) Date of Patent: *Feb. 14, 2012

(54) CLAMPING PIN

(75) Inventors: Christian Steiner, Eisenach (DE);
Meinrad Fiechter, Münsingen (CH);
Beat Knuchel, Ursenbach (CH);
Vinzenz Burgherr, Wabern (CH)

(73) Assignee: Stryker Trauma SA (CH)

( * ) Notice: Subject to any disclaimer, the term of this patent is extended or adjusted under 35 U.S.C. 154(b) by 653 days.

This patent is subject to a terminal disclaimer.

(21) Appl. No.: 12/288,328

(22) Filed: Oct. 17, 2008

(65) Prior Publication Data
US 2009/0198236 A1 Aug. 6, 2009

(30) Foreign Application Priority Data
Feb. 1, 2008 (EP) ..................................... 08150944

(51) Int. Cl.
*A61F 5/04* (2006.01)
*F16B 7/10* (2006.01)
*F16B 2/14* (2006.01)

(52) U.S. Cl. ...................... 606/59; 403/109.5; 403/374.1

(58) Field of Classification Search .................. 606/59; 403/109.1, 109.5, 109.8, 136, 191, 248, 325, 403/367, 368, 374.1, 409.1; 285/33, 121.2
See application file for complete search history.

(56) References Cited

U.S. PATENT DOCUMENTS

| | | | |
|---|---|---|---|
| 2,291,747 A * | 8/1942 | Neuwirth | 248/188.5 |
| 2,883,219 A * | 4/1959 | Cox | 403/105 |
| 3,691,788 A | 9/1972 | Mazziotti | |
| 3,977,397 A | 8/1976 | Kalnberz et al. | |
| 4,308,863 A | 1/1982 | Fischer | |
| 4,520,983 A | 6/1985 | Templeman | |
| 4,615,338 A | 10/1986 | Ilizarov et al. | |
| 4,978,348 A | 12/1990 | Ilizarov et al. | |
| 5,087,258 A | 2/1992 | Schewior | |

(Continued)

FOREIGN PATENT DOCUMENTS

EP 0377744 7/1990

(Continued)

OTHER PUBLICATIONS

European Search Report, EP 08 15 0944.

(Continued)

*Primary Examiner* — Eduardo C Robert
*Assistant Examiner* — Jacqueline Johanas
(74) *Attorney, Agent, or Firm* — Lerner, David, Littenberg, Krumholz & Mentlik, LLP (57) ABSTRACT

A clamping pin is intended to be inserted into and held in an opening of a medical device. The clamping pin comprises a screw having a longitudinal axis, a first clamping element having a surface inclined to the longitudinal axis and provides a first part of a clamping section. A second clamping element has a surface inclined to the longitudinal axis and provides a second part of the clamping section which is complementary to the opening in the medical device. The inclined surfaces of the first and second clamping elements are in contact. A screw extends at least partly through both the first and second clamping elements. The screw engages in one of the clamping elements such that the axial distance between the two clamping elements and the diameter of the clamping section that can come in contact with a surface of the opening in the medical device will be changed upon actuation of the screw.

13 Claims, 8 Drawing Sheets

U.S. PATENT DOCUMENTS

| | | | |
|---|---|---|---|
| 5,466,237 | A | 11/1995 | Byrd, III et al. |
| 5,702,389 | A | 12/1997 | Taylor et al. |
| 5,728,095 | A | 3/1998 | Taylor et al. |
| 5,863,292 | A | 1/1999 | Tosic |
| 6,021,579 | A | 2/2000 | Schimmels et al. |
| 6,030,386 | A | 2/2000 | Taylor et al. |
| 6,090,111 | A | 7/2000 | Nichols |
| 6,176,860 | B1 | 1/2001 | Howard |
| 6,371,957 | B1 | 4/2002 | Amreim et al. |
| 6,565,565 | B1 | 5/2003 | Yuan et al. |
| 6,565,567 | B1 | 5/2003 | Haider |
| 6,701,174 | B1 | 3/2004 | Krause et al. |
| 6,733,502 | B2 | 5/2004 | Altarac et al. |
| 7,022,122 | B2 | 4/2006 | Amreim et al. |
| 7,197,806 | B2* | 4/2007 | Boudreaux et al. ............. 29/434 |
| 7,282,052 | B2 | 10/2007 | Mullaney |
| 7,306,601 | B2 | 12/2007 | McGrath et al. |
| 7,377,923 | B2 | 5/2008 | Purcell et al. |
| 7,422,593 | B2 | 9/2008 | Cresina et al. |
| 2001/0025181 | A1 | 9/2001 | Freedlan |
| 2002/0010465 | A1 | 1/2002 | Koo et al. |
| 2003/0063949 | A1* | 4/2003 | Hohenocker ................. 403/367 |
| 2005/0015087 | A1 | 1/2005 | Walulik et al. |
| 2005/0084325 | A1 | 4/2005 | O'Brien et al. |
| 2005/0248156 | A1* | 11/2005 | Hsieh ........................ 285/397 |
| 2005/0251136 | A1 | 11/2005 | Noon et al. |
| 2006/0184169 | A1 | 8/2006 | Stevens |
| 2006/0243873 | A1* | 11/2006 | Carnevali ................. 248/288.31 |
| 2006/0247622 | A1 | 11/2006 | Maughan et al. |
| 2006/0247629 | A1 | 11/2006 | Maughan et al. |
| 2006/0261221 | A1 | 11/2006 | Carnevali |
| 2007/0162022 | A1 | 7/2007 | Zhang et al. |
| 2008/0021451 | A1 | 1/2008 | Coull et al. |
| 2009/0198235 | A1* | 8/2009 | Steiner et al. .................. 606/57 |
| 2010/0087819 | A1 | 4/2010 | Mullaney |

FOREIGN PATENT DOCUMENTS

| | | |
|---|---|---|
| EP | 1016381 | 12/2003 |
| FR | 2439002 | 5/1980 |
| FR | 7829405 | 5/1980 |
| FR | 2576774 | 8/1986 |
| FR | 2756025 A1 | 5/1998 |
| IT | 1259768 | 3/1996 |
| WO | WO-01/78613 | 10/2001 |

OTHER PUBLICATIONS

Alizade et al., Mech. Mach. Theory, vol. 29, No. 1, pp. 115-124, 1994, Great Britain.

European Search Report, EP 08 15 0971.

European Search Report, EP 09 15 0507.

International Search Report and Written Opinion, PCT/US2010/000712, dated Jun. 28, 2010.

Smith&Nephew, Taylor Spatial Frame, website printout, Aug. 12, 2009.

* cited by examiner

CLAMPING PIN

BACKGROUND OF THE INVENTION

The invention relates to a clamping pin for use in an external fixation system for adjustment of a bone fracture.

The prior art teaches several locking mechanism or clamping elements to connect a cylindrical element with a frame of an external fixation system via an opening that is arranged within the frame. Such frames can have different shapes, for example the shape of a circle, a segment of a circle, rectangular etc. and enclose a limb of human body at least partly.

U.S. Pat. No. 5,681,309 discloses a distraction apparatus comprising two rings to which pins are attachable. The pins provide a connection between bony structure and the rings of the external fixator. The two rings are connected by means of several rods. The length of the rods is adjustable in order to adjust the position of the two rings relative to each other. Each ring comprises a plurality of openings into which the rods can be introduced. The rods are fixed to the ring by means of a locking mechanism comprising a nut and a bolt. In order to connect the rod with the ring two nuts (one on each side of the ring) are used and tightened against each other. The assembly comprises further a functional element such as a holder of a pin that is connected to a bone fragment.

The handling of bolts and nuts is cumbersome for the medical practitioner as a tool has to be used on both sides of the ring. Additionally the medical practitioner has to handle two elements, namely the bolt and the nut. Due to that it may be likely that some of the elements may fall down. Furthermore the accurate positioning is also rather troublesome as the position of the ring usually shifts slightly when the nuts will be tightened securely.

A pin holder is shown in U.S. Pat. No. 6,342,054 and in a U.S. patent application Ser. No. 12/288,332 having the same filing date as this application and listing Christian Steiner, Meinrad Fiechter, Beat Knuchel and Vinzenz Burgherr as inventors.

SUMMARY OF THE INVENTION

One aspect of the present invention is to provide a clamping pin, which overcomes the disadvantages of prior art. In particular the connecting process of the clamping pin with an opening of an external fixation system shall be in an easy manner.

According to the invention there is provided a clamping pin being intended to be inserted into and held in an opening of a medical device. The clamping pin comprises a screw having a longitudinal axis, a first clamping element having an inclined surface that is inclined to the longitudinal axis and providing a first part of a clamping section, and a second clamping element having an inclined surface that is inclined to the longitudinal axis and providing a second part of the clamping section which clamping section is complementary to the opening. The inclined surface of the first clamping element is in contact with the inclined surface of the second clamping element. The screw extends at least partly through the second clamping element and at least partly through the first clamping element, which screw engages in one of the clamping elements such that the axial distance between the clamping pins and the diameter of the clamping section that can come in contact with the surface of the opening will be changed upon actuation of the screw.

Such a clamping pin can be inserted into an opening of a medical device very easily. Also the tightening process can be conducted in an easily manner.

In a further embodiment the screw extends completely through the first clamping element and through the second clamping element such that the screw may be in an engagement with a further element.

The clamping pin comprises preferably a spring, which is arranged such that it provides an axial force onto one of the clamping elements such that the clamping element is pushed against the other clamping element.

The arrangement of the spring is particularly advantageous as an axial and radial displacement of said clamping elements results. When the clamping pin is arranged within an opening the displacement is limited by the sidewall of the opening resulting in a radial force holding the clamping pin in position. Furthermore the axial force prevents a rattling resulting from the two clamping elements.

Preferably the clamping pin comprises a spring, which is arranged such that it provides an axial force onto one of the clamping elements such that the clamping element is pushed away from the other clamping element. Such an embodiment is particularly advantageous to provide a connection between two medical devices.

The spring is preferably arranged within a spring cavity that is provided by an opening in one of the clamping elements. The first clamping element has preferably a substantially equal-shaped cross-section as viewed perpendicular to the axis as the second clamping element.

Preferably the cross-section of the clamping elements is circular, rectangular, quadratic, elliptical or polygonal. However, any other forms are also possible as long as they are complementary to the cross-section of the opening.

Preferably at least one of the clamping elements comprises elements protruding over the circumferential surface or into the circumferential surface, wherein said elements can be used to move said clamping element against or away from the other clamping element.

BRIEF DESCRIPTION OF THE DRAWINGS

The drawings will be explained in greater detail by means of a description of an exemplary embodiment, with reference to the following figures.

DETAILED DESCRIPTION

Figure 1:
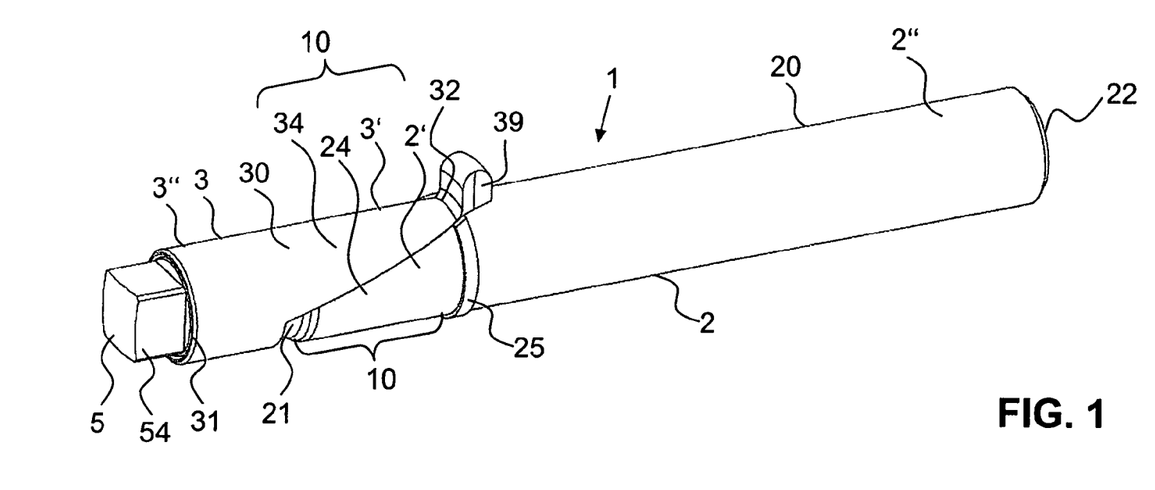
FIG. 1 shows a perspective view of a clamping pin according to a first embodiment of the present invention.
Figure 2A:
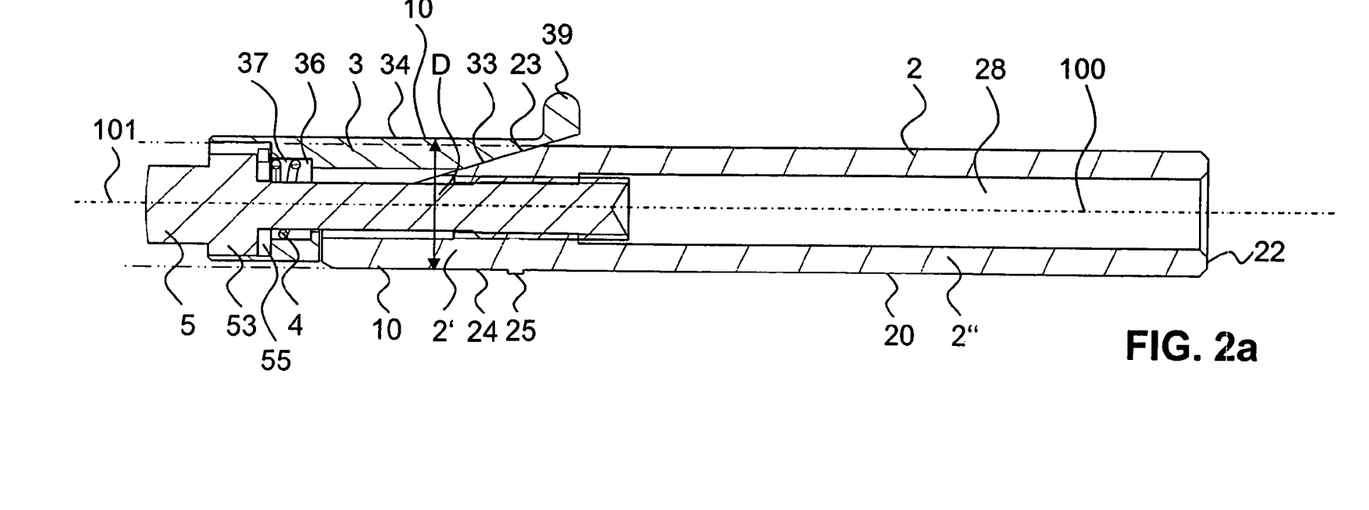
FIG. 2a shows a section view of a clamping pin according to FIG. 1 in a stationary position.
Figure 2B:
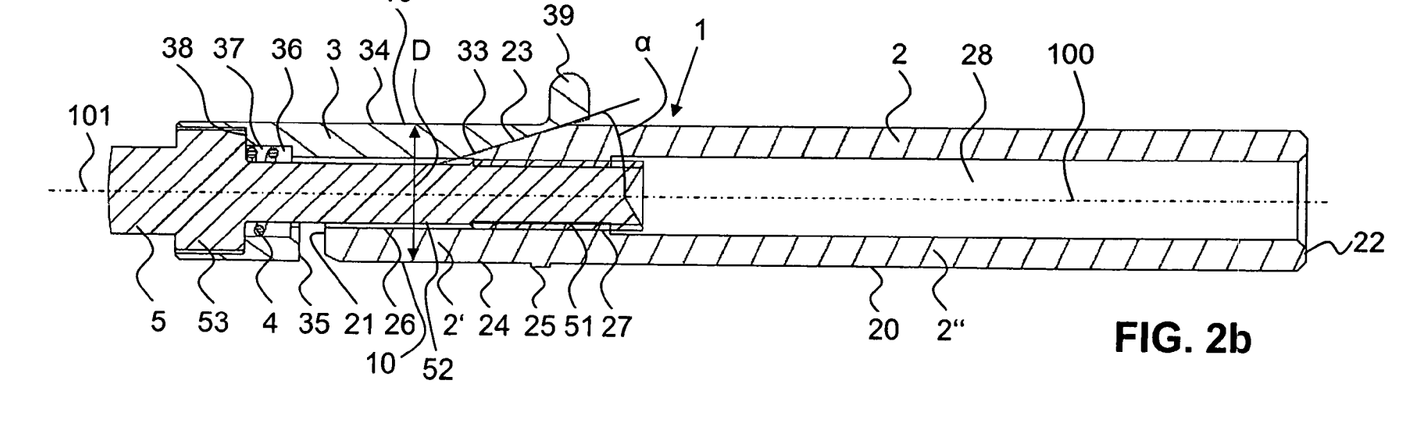
FIG. 2b shows a section view of a clamping pin according to FIG. 1 in an inserting position.
Figure 2C:
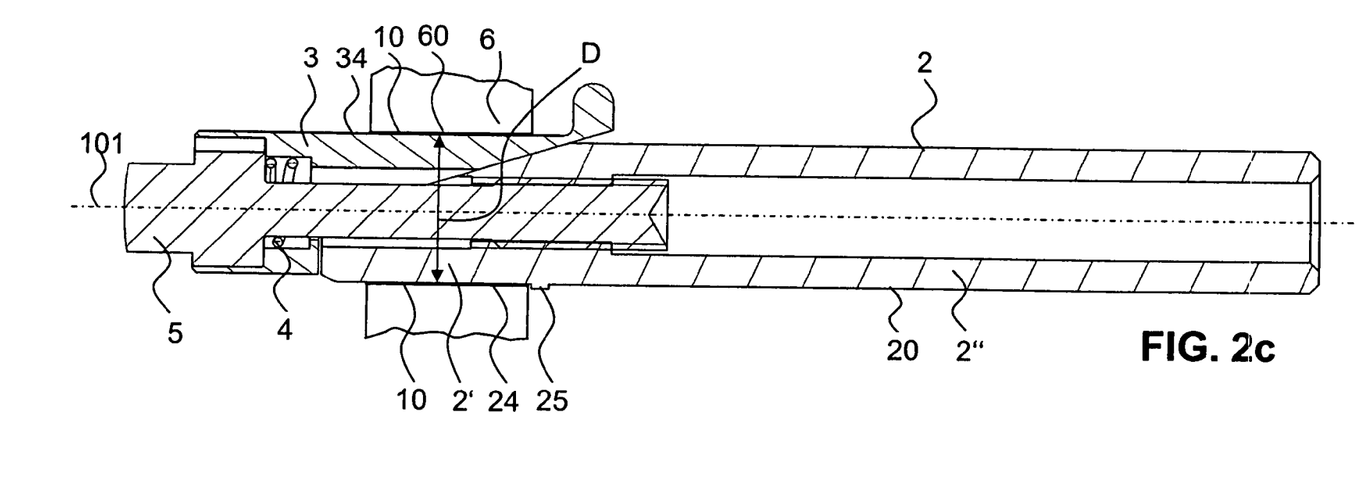
FIG. 2c shows a section view of a clamping pin according to FIG. 1 in a tightened position.
Figure 3:
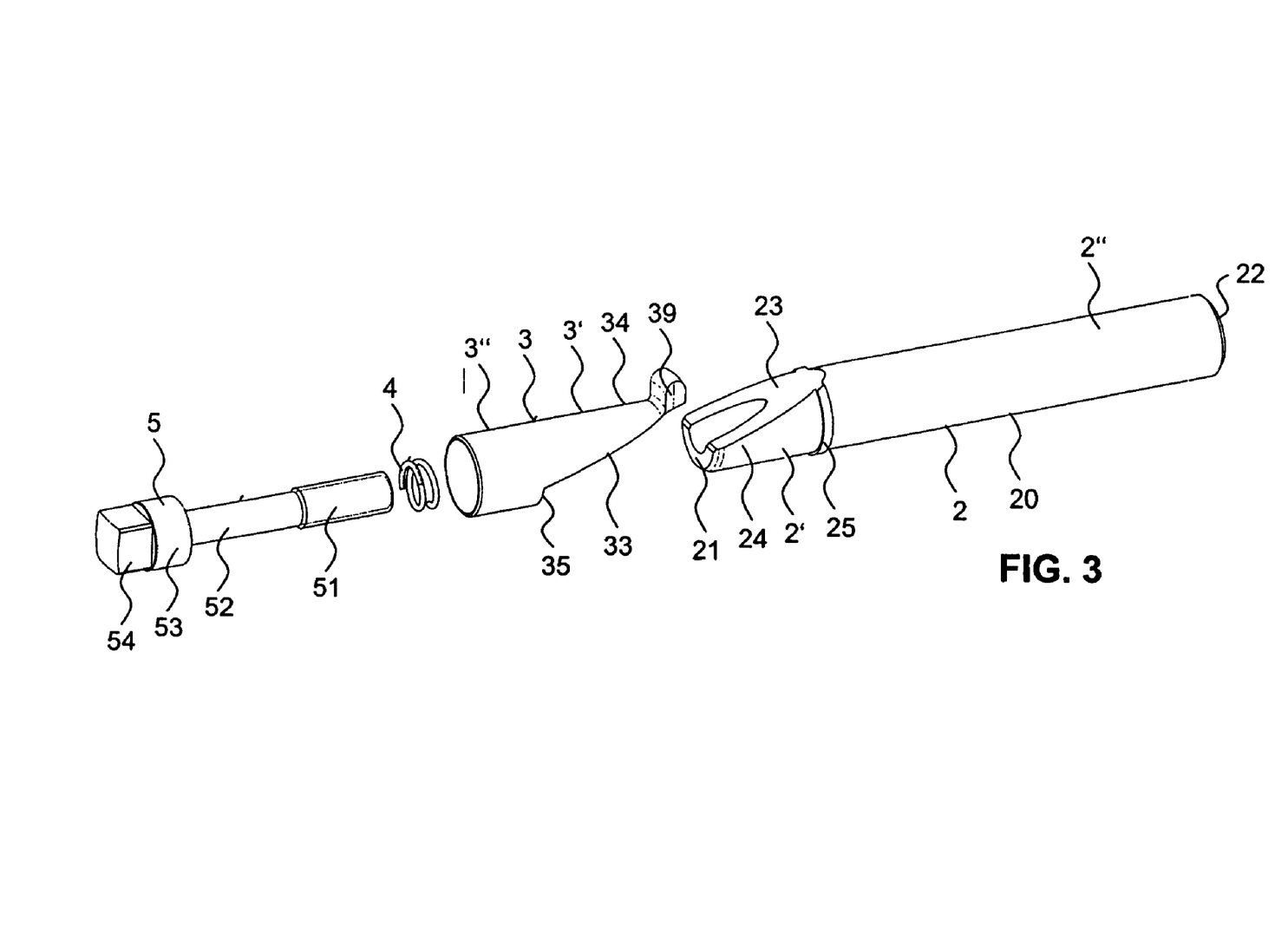
FIG. 3 shows an exploded view of a clamping pin according to FIG. 1.

FIGS. 1 to 3 show different views of a clamping pin 1 according to a first embodiment of the present invention. The clamping pin 1 can also be designated as locking device or locking mechanism. The clamping pin 1 according to the present invention is used to be inserted and held firmly in an opening of a medical device such as for example an external fixation device for bone adjustment after a fracture. The clamping pin 1 is designed such for being introduced into an opening of the external fixation device and for being securely fixed within said opening.

The clamping pin 1 comprises a first clamping element 2, a second clamping element 3, an optional spring 4 and a screw 5. The clamping pin 1 comprises furthermore a clamping section 10 which is in contact with an opening of said medical device (e.g. a fixation device such as a ring, plate etc.). Clamping section 10 is actually provided by means of the first clamping element 2 and the second clamping element 3. The first clamping element 2 and the second clamping element 3 are arranged such that upon rotation of the screw 5 the axial distance between the two clamping elements 2, 3 can be adjusted, due to the axial displacement, and a radial displacement which is the result of the axial displacement and the design of the first clamping element 2 and the second clamping element 3, the dimension or width D (e.g. the maximal diameter) of the clamping pin 1 at the location of the clamping section 10 can be varied. Due to the radial extension of the clamping section 10 a radial force against the surface of the opening is provided such that the clamping 1 is held by the radial force.

The first clamping element 2 has the shape of a cylinder that extends along a longitudinal axis 100. The cylinder comprises a circumferential surface 20 and two end faces 21, 22. The cross sectional area, i.e. the end faces 21, 22, of the cylinder has preferably the shape of a circle as it is illustrated in the FIGS. 1 to 3. Depending on the openings in the medical device the cross sectional area may have any other shape such as elliptical, polygonal, rectangular or quadratic.

The first clamping element 2 comprises a clamping section 2' and a functional section 2". The clamping section 2' is in contact with the opening of the fixation element, whereas the functional section 2" is provided for the attachment of a pin or any other device to the clamping pin 1. Examples are described below.

The clamping section 2' comprises an inclined surface 23 which is arranged angular to the longitudinal axis 100. Inclined surface 23 extends preferably from the section point of the longitudinal axis 100 and the end face 21 in an angle α along the longitudinal axis 100. Preferably the angle is between 5° and 45°, especially between 10° and 20°. Therefore the inclined surface 23 interrupts the circumferential surface 20 of the first clamping section 2'. The remaining part of the circumferential surface 20 forms a first part 24 of the above mentioned clamping section 10. In axial direction the first part 24 of clamping section 10 is limited by an embossment 25. Embossment 25 extends radially above surface 20.

Referring to FIG. 3, the inclined surface 34 is provided as a plane surface. A plane surface is to be understood as a surface wherein all surface elements lie in a common plane. Providing the surface 23 as plane surface has the advantage that the element which provides the features to allow a change in diameter is fully integrated in the clamping element and no additional element such as conical rings have to be arranged in order to provide a change in diameter which may be used to clamp the clamping element according to the description above. The outer surface of first part 24 of the clamping section 10 being in engagement with the opening of the medical device has a substantially circular form as viewed along the central axis 100, i.e. is part-cylindrical. Thus the clamping section 2' of the first clamping element 2 is provided by means of a first part 24 having the part-spherical form and inclined plane surface 23.

An opening 26 extends along axis 100 through clamping section 2' of first clamping element 2. This can be seen in FIG. 2. The opening comprises a thread 27 with which the screw 5 is engaged.

The functional section 2" here is shaped as a hollow cylinder having an outer surface onto which any medical device such as a clamping element can be fixed. Therefore the first clamping element 2 comprises a further opening 28 extending through the further section 2". Further opening 28 has a larger diameter than the opening 26.

The preferred second clamping element 3 has the shape of a cylinder that extends along a longitudinal axis 101. It has to be noted that when the second clamping element 3 is arranged with respect to the first clamping element 2 such that the clamping section 10 has a circular shape, the longitudinal axis 101 is collinear to the longitudinal axis 100. The cylinder comprises a circumferential surface 30 and two end faces 31, 32. The cross sectional area of the cylinder has preferably the same shape as the one of the first clamping element 2.

The second clamping element 3 comprises a clamping section 3' and a fixing section 3".

The clamping section 3' comprises an inclined surface 33 which is arranged angular to the longitudinal axis 100. In the present embodiment the inclined surface 33 is arranged such that the end face 32 is rather small. Inclined surface 33 is arranged such that it forms a counterpart to the inclined surface 23 of the first clamping element 2. As above, the inclined surface 33 interrupts the circumferential surface 30 of the first clamping section 3'. The remaining part of circumferential surface 30 forms a second part 34 of the above mentioned clamping section 10. In axial direction the second part 34 of clamping section 10 is limited by a shoulder 35 that extends perpendicular to the longitudinal axis 101. As it can be seen from the cross sectional view of FIG. 2 the inclined surface 23 of the first clamping element 2 is in contact with the inclined surface 33 of the second clamping element 3.

The inclined surface 33 is provided as a plane surface. Providing the surface 33 as plane surface has the advantage that the element which provides the features to allow a change in diameter is fully integrated in the clamping element and no additional elements such as conical rings have to be arranged in order to provide a change in diameter which may be used to clamp the clamping element according to the description above. The second part or surface 34 of the clamping section 10 being in engagement with the opening of the medical device has a substantially circular cross-sectional form as viewed along the central axis 100, i.e. is part-cylindrical. Thus, the clamping section 3' of the second clamping element 3 is provided by means of a surface 34 having a circular form and an inclined plane surface 33.

The second clamping element 3 comprises furthermore an opening 36 extending along the longitudinal axis 101 through the second clamping element 3. The opening 36 is adapted to receive the spring 4 and parts of the screw 5. The diameter of the opening 36 is larger in a first portion close to the end face 31 than the diameter in a second portion that is adjacent to the first portion. Thereby a shoulder 38 is provided. In a third portion that is close to the shoulder 35 the diameter is smaller than the diameter in the second portion. Thereby the opening 26 provides in its second portion a spring cavity 37 that is limited by the opening 36 and parts of the screw 5.

Additionally the second clamping element 3 comprises a notch 39. The notch 39 is attached to the clamping section 3' at the end face 32 and protrudes over the second part 34 of the clamping section 10 in radial direction, such that the medical practitioner is able to grasp notch 39 or push the notch 39 away from the functional section 2" to separate the second clamping element 3 in axial movement from the first clamping element 2. Thereby the diameter of the clamping section 10 becomes smaller such that medical practitioner can introduce the clamping pin 1 into a corresponding opening. As soon as the medical practitioner releases notch 39 the first clamping element 2 and the second clamping element 3 will be actuated by means of the spring 4 such that both clamping elements 2 and 3 will be pushed with the respective clamping surface against the opening of the medical device. In this position the diameter of the clamping section is larger than the diameter of the opening such that a force from clamping section 10 is applied onto the surface of the opening within the medical device. This force serves as a biasing force which holds the clamping pin within the opening.

FIGS. 2 and 3 show also the spring 4 which is a compression spring with several windings. The spring 4 provides a force in axial direction onto the second clamping element 3 via the shoulder 53 of the screw 5. The impact and the function of the spring 4 will be explained below. Generally the spring 4 can also be designated as a biasing device which provides a biasing force from the clamping pin 1 via its clamping section 10 to the opening of a medical device as the force in axial direction is converted by means of the inclined surfaces to a force perpendicular to the middle axis.

The screw 5 comprises a threaded portion 51, a shaft portion 52, a shoulder portion 53 and a head portion 54. The threaded portion 51 is designed such that it is engageable with the thread 27 of the first clamping element 2. The shaft portion 52 connects the threaded portion 51 to the shoulder portion 53. The shoulder portion 53 has a larger diameter than the shaft portion 52 and the threaded portion 51. The head portion 54 is formed onto the shoulder portion 53 and comprises means in which a tool is engageable such that the screw can be actuated. In the preferred embodiment the head portion 54 has the shape of a four-cornered shaft. However, other shapes such as a hexagon socket may also be provided.

The screw 5 extends in the present embodiment completely through the second clamping element 3 and partly into the first clamping element 2. Generally, the screw 5 extends at least partly into or through the second clamping element 3 and at least partly into or through the first clamping element 2. This means that the screw 5 may be arranged such that it does not extend over the first clamping element 2 and the second clamping element 3 in axial direction, which means that the screw is not visible from the outside as it is fully integrated in the clamping elements 2, 3. In other embodiments the screw 5 may be arranged such that it extends completely through one clamping element. Such an embodiment is shown in FIG. 2a, wherein the screw extends completely through and in axial direction beyond (here with the head portion 54) the second clamping element 3. In other embodiments it may also be possible that the screw 5 extends completely through and beyond the first clamping element 2. In a still further embodiment the screw is arranged such that it extends completely through both clamping elements 2, 3.

The clamping pin 1 according to the present invention can adopt four different positions:

a) a stationary position as shown in FIG. 2a (the width D of the clamping surface 10 is thereby larger than the diameter of the opening in the medical device);

b) a inserting position in order to introduce the clamping pin into an opening as shown in FIG. 2b (the width D is thereby smaller or equal to the diameter of the opening in the medical device);

c) a spring-biased position in order to secure the clamping pin within the medical device opening in a pre-biased manner. Such a position has the advantage that the clamping pin can be inserted into the opening and is held due to effect of the spring. This position is achieved after the insertion of the clamping pin 1 into the opening when the clamping section 10 is in connection with the surface of the opening 60 and when the screw 5 is not actuated. This position provides the advantage that the medical practitioner can introduce the clamping pin 1 into the opening 60 and upon releasing the force via the notch 29 against the force provided by the spring 4 only the spring force is present and moves the second clamping element 3 against the first clamping element 2. Due to this movement diameter D increases and a radial force is exerted from the clamping section 10 onto the opening 60. The radial force originating from the spring force being converted, via the inclined surfaces, into a radial force.

d) a tightened position in order clamp the claming pin with said opening as shown in FIG. 2c (the width D in that position is equal to the diameter of the opening in the medical device).

FIG. 2a shows the stationary position. The screw is arranged such that the head portion 53 is not in contact with the shoulder 38. Between shoulder 38 and head portion 53 is therefore a gap 55. However, the screw 5 may also be arranged relative to the second clamping element 3 so that shoulder portion 53 is in contact with the shoulder 38. As a result the spring 4 expands and provides a force from the shoulder portion 53 of the screw 5 to the second clamping element 3. Therefore the second clamping element 3 is pushed against the first clamping element 2.

FIG. 2b shows the inserting position. The elements are preferably designed such that the diameter D of the clamping section 10 is larger than the diameter of the functional section 2". If the user wants to introduce the clamping pin 1 according to the present invention into an opening element of an external fixator, he/she has to provide a force against the force of the spring 4 in order to minimize the dimension of diameter D of the clamping section 10. Such a force is preferably applied over notch or lug 39. This means that the second clamping element 3 has to be moved against the force of the spring 4. As soon as the clamping pin 1 has been introduced into the opening, the user can release its force and the clamping pin will be retained loosely in the opening as the spring provides an axial force resulting in an expansion of the diameter D.

FIG. 2c shows the inserted and fixed position. Thereby clamping pin 1 is arranged in an opening 60 of medical device 6 which are both shown in a schematic manner. In order to provide a secure and fixed connection between the clamping pin 1 and the external fixation element, the user has to actuate the screw 5. The screw 5 has to be actuated such that the shoulder portion 53 comes in contact with the shoulder 38. Further actuation results in an axial and radial movement of the first clamping element 2 with respect to the second clamping element 3. The movement in radial direction is due to the fact that the first clamping element 2 and the second clamping element 3 move along the inclined surfaces 23, 33. Due to radial movement, the diameter of the clamping section 10 will be increased, which leads to a clamp connection between an opening 60 of an external fixator and the clamping pin 1 according to the present invention. This means that the first part 24 and the second part 34 of the clamping surface 10 are in an engagement with the surface 60 of the medical device 6. Surface 20 will not be in alignment with surface 30 in the clamping section 10 in that position. It has to be mentioned that the first clamping element 2 and the second clamping element 3 or the respective clamping sections 2', 3' can comprise any other cross-sectional shape and are not limited to circles or parts of a circle. If the opening within the medical device is rectangular, then the cross-section of the clamping section 10 has to be rectangular as well. This means that the cross-section of at least the clamping section 10 of the first clamping element 2 and the second clamping element 3 has to be complementary to form of the opening in the medical device.

Figure 4:
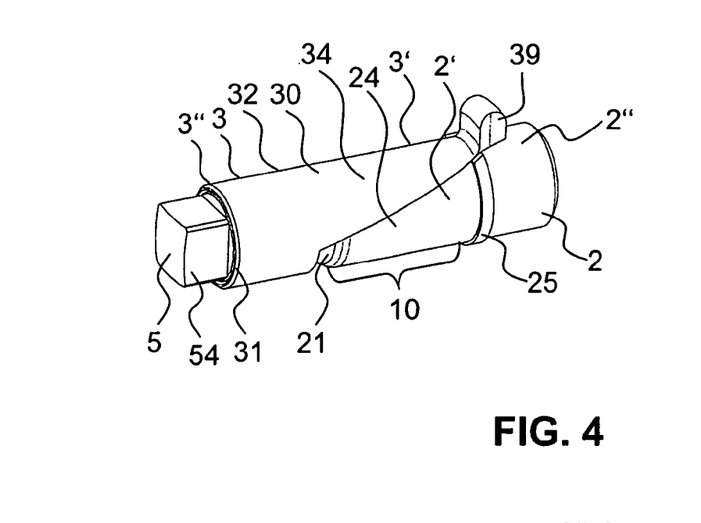
FIG. 4 shows a perspective view of a clamping pin according to a second embodiment of the present invention.
Figure 5:
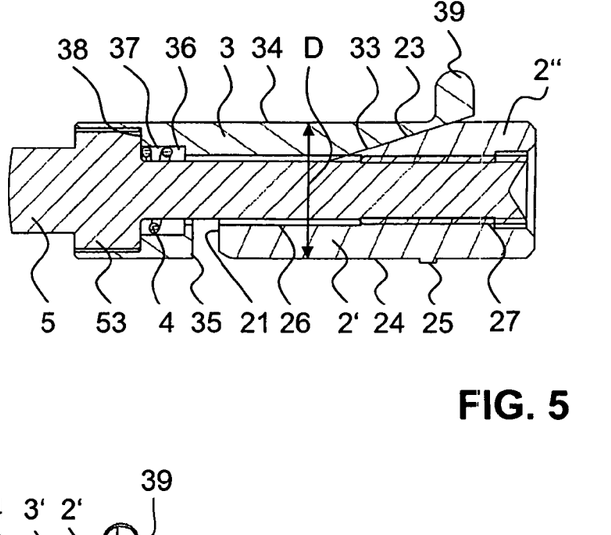
FIG. 5 shows a section view of a clamping pin according to FIG. 4.
Figure 6:
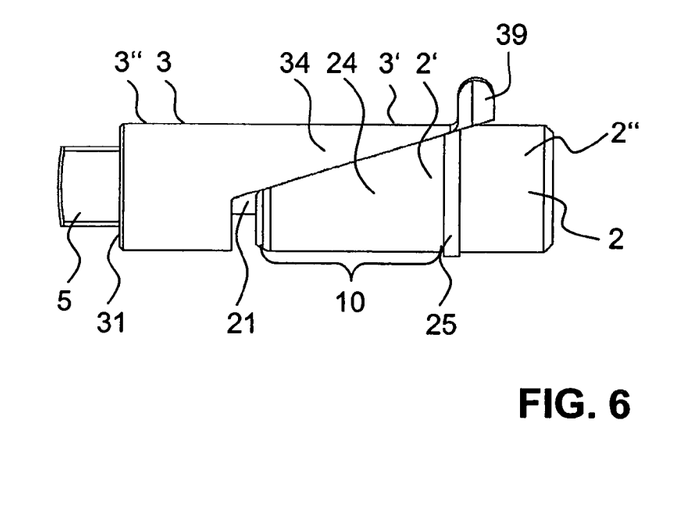
FIG. 6 shows an explosion view of a clamping pin according to FIG. 4.

FIG. 4 to FIG. 6 show a second embodiment of a clamping pin 1, according to the present invention. It has to be noted that various features of all embodiments as described herein may be combined to make new embodiments. The embodiment shown in said figures will also be designated as shorter version as the functional part 2" has a shorter length in axial direction as the functional part of the first embodiment. This means that any appendix could be used in prolongation of functional section 2". Throughout the application, the same reference numeral are provided for the same features.

Figure 7:
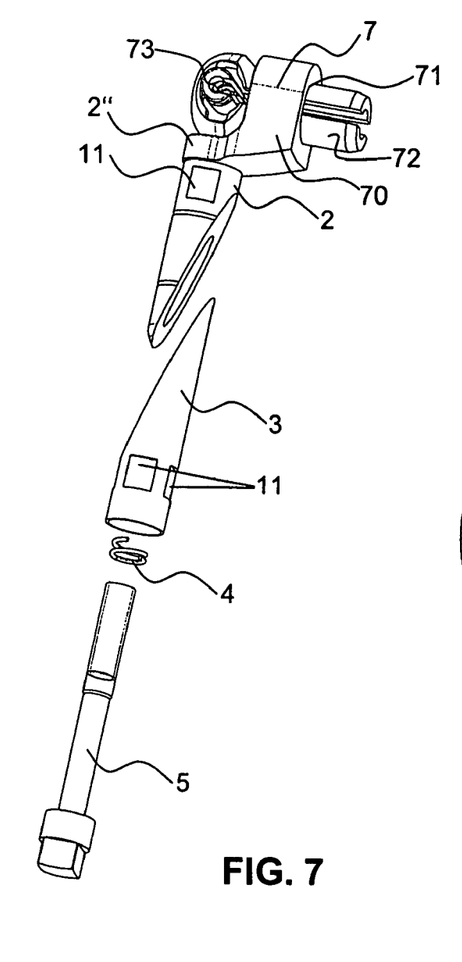
FIG. 7 shows a perspective view of a clamping pin according to the present invention with a holder of a wire post.
Figure 8:
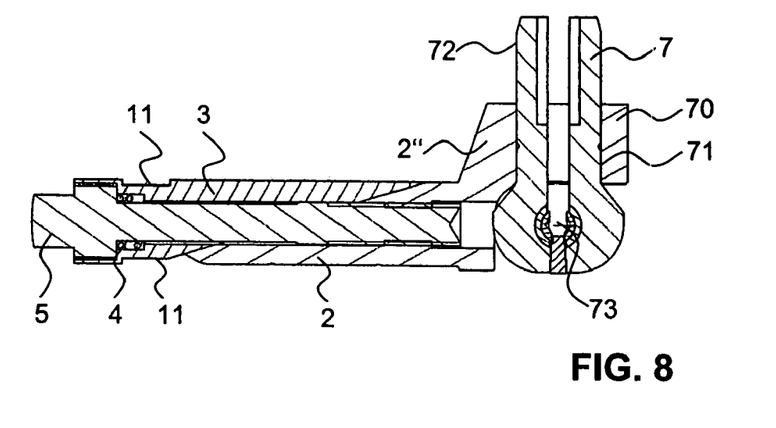
FIG. 8 shows a section view of FIG. 7.

FIG. 7 and FIG. 8 show a further embodiment of a clamping pin 1. In this embodiment the functional section 2" comprises a holder 70 for a wire post 7. The wire post 7 is used to hold a wire that is in connection with a bony structure. The first clamping element 2 and the second clamping element 3 in that embodiment comprise several plane surfaces 11 instead of a notch. The gripping surfaces 11 are arranged in pairs preferably on opposite sides in respect of the middle axis. However, the gripping surfaces 11 can also be arranged in any angle with respect to each other, such that a tool is engageable. Due to such an arrangement the gripping surfaces 11 are enabled to be in an engagement with a tool such as wrench. The medical practitioner therefore is able to grasp the first clamping element 2 and the second clamping element 3 by means of two tools that engage with the gripping surfaces 11 of the clamping elements 2, 3. The medical practitioner simply turns the tools with respect to each other against the force provided by spring 4 in order to bring the clamping pin 1 from the stationary position to the inserting position. Once the clamping pin 1 is positioned within an opening of a medical device, it can be fixed by actuating screw 5.

The wire post is arranged within a holder 70 that adjoins the functional section 2" of the first clamping element 2. The holder 70 comprises an opening 71 in which the cylindrical section 72 of the wire post is arranged. The opening 71 is arranged perpendicular to the main axis of the first clamping element 2. However, it can be arranged in any other angle with respect to the main axis. The wire post 7 is arranged such that it is rotatable with respect to the holder 70 in order to position the rod or wire that is arranged in a wire opening 73.

Figures 9, 10:
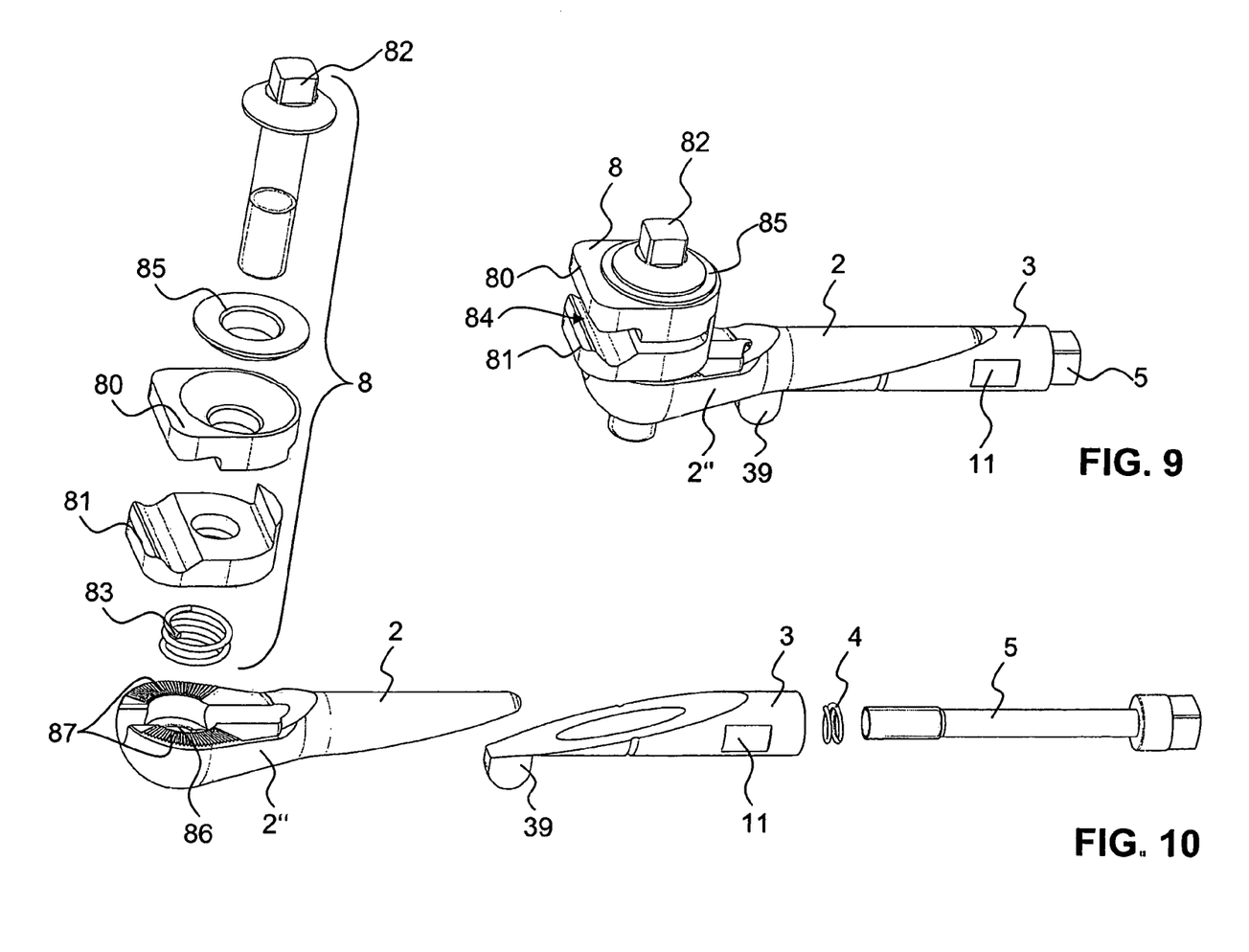
FIG. 9 shows a perspective view of a clamping pin according to the present invention with a clamping element.
FIG. 10 shows an exploded view of FIG. 9.
Figure 11:
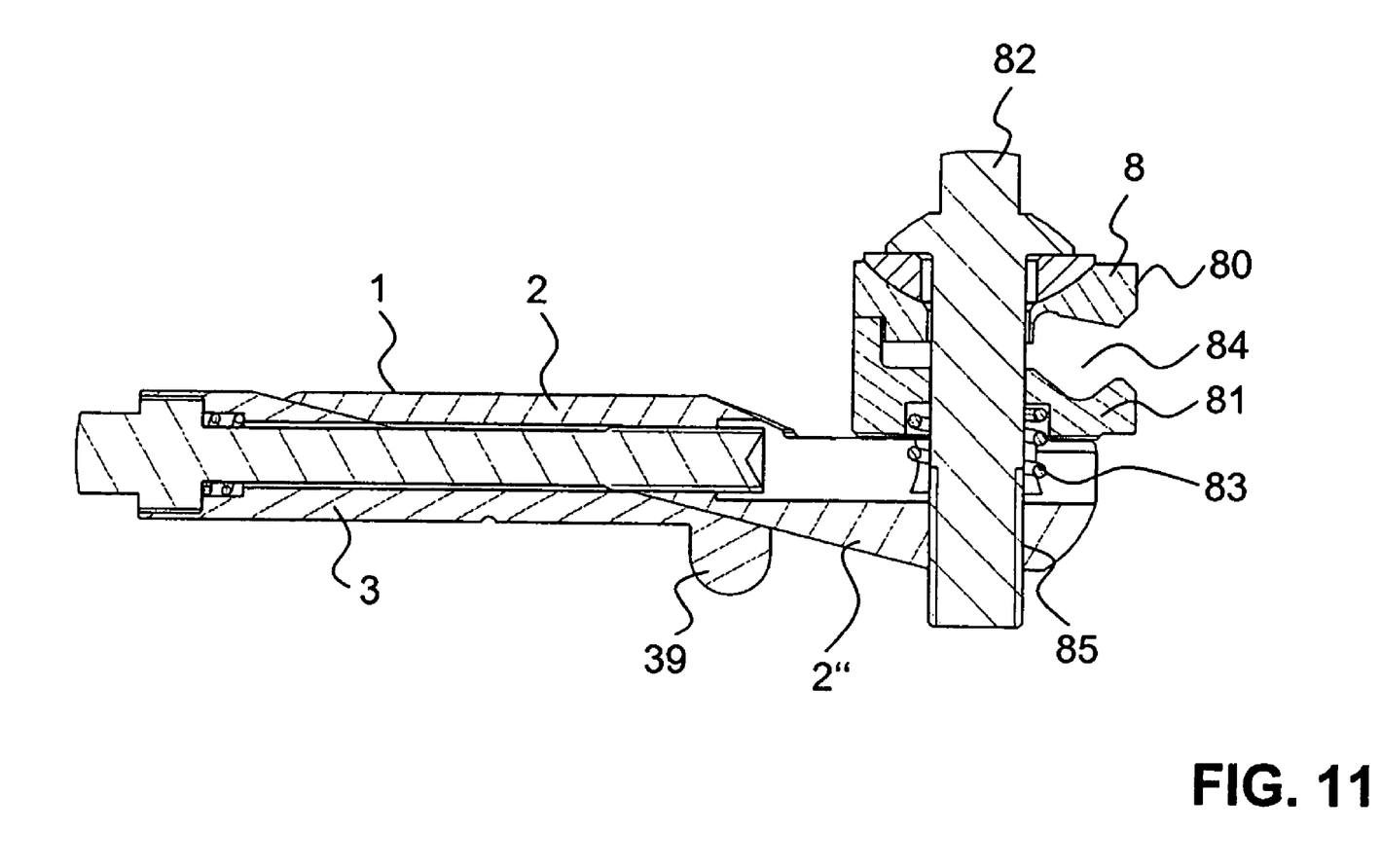
FIG. 11 shows a section view of FIG. 9.
Figure 12:
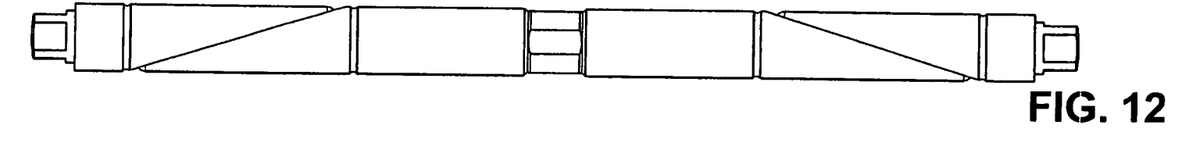
FIG. 12 shows a view of a clamping arrangement comprising two clamping pins according to a further embodiment of the present invention.
Figure 13:
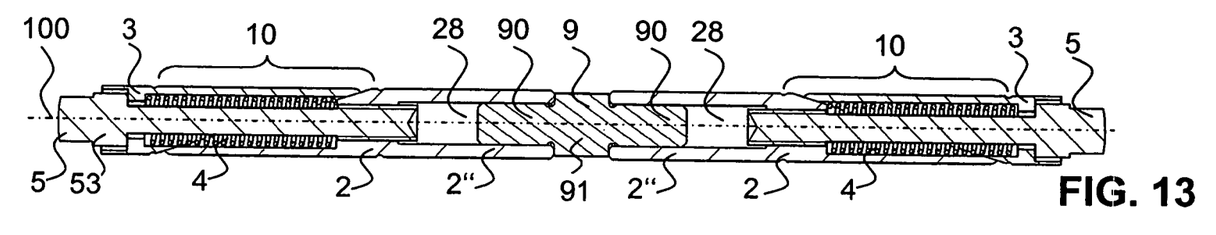
FIG. 13 shows a section view of FIG. 12.
Figures 14, 15:
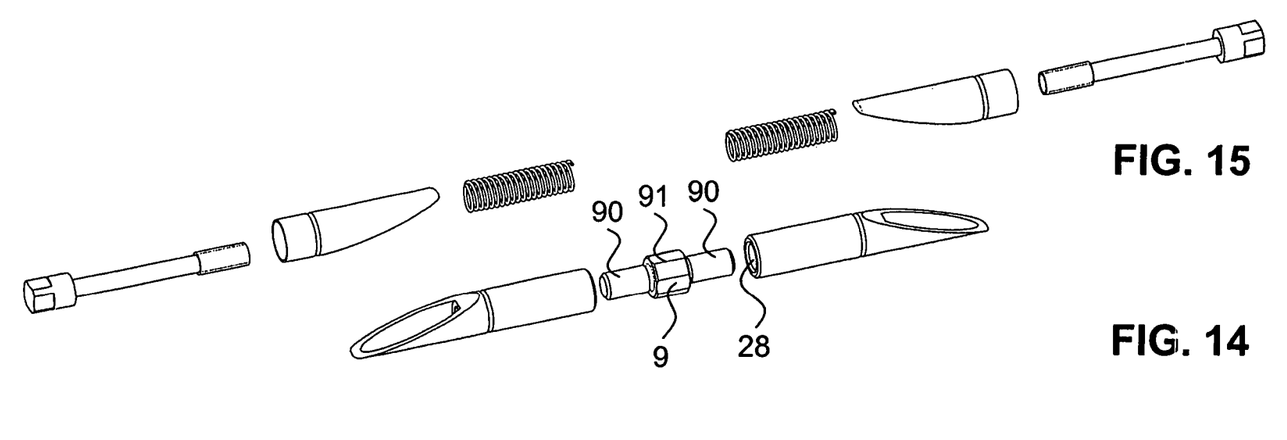
FIG. 14 shows an exploded view of FIG. 12.
FIG. 15 shows a further exploded view of FIG. 12.

FIG. 9 to FIG. 11 show a clamping pin 1 according to the present invention, wherein the functional section 2" comprises a jaw element 8 to clamp a pin or a rod. The jaw element 8 comprises two clamp jaws 80, 81, a screw 82, a spring 83 and a washer 85. The two clamp jaws 80, 81 provide a receptacle space 84 which can take up a pin or a rod. Upon actuation of the screw 82, the two clamp jaws 80, 81 will be moved together along the axial direction of the screw 82 and the pin which is arranged in the receptacle space 84 will be clamped within the two clamp jaws 80, 81. The screw 82 itself engages in a threaded opening 86 that is arranged in the functional part 2" of the first clamping element 2 and extends through both clamping jaws 80, 81 and the washer 85. The threaded opening 86 is arranged angular to the longitudinal axis 100 of the second clamping element 2. In the present embodiment, the angle is 90°, but it can have any other angle. A flange 87 extends partially around the threaded opening 86. Said flange 87 provides a contact surface for the clamp jaw 81. The contact surface on the flange 87 as well as the respective on the clamp jaw 81 can comprise a toothed structure, whereby the teeth of the flange 87 engage in the teeth of the clamp jaw 81. Thereby the medical practitioner is able to adjust the position of clamp jaws 80, 81 with respect to the main axis of the first clamping element 2 in a steplike manner.

The second clamping element 3 according to that embodiment shows a combination of possible actuation elements by means of which the medical practitioner is able to bring the clamping pin 1 from the stationary position to the inserting position. Thereby the second clamping element 3 can comprise the notch 39 which can be actuated by hand, and the gripping surfaces 11 which can be actuated by wrench or any other suitable tool.

FIG. 12 to FIG. 15 show an arrangement of two clamping pins according to the present invention, whereby the functional section 2" of the first clamping element 2 comprises an opening 28 that extends along the longitudinal axis 100. The arrangement further comprises a connection module 9. Connection module 9 comprises two outer sections 90 and a middle section 91.

The clamping pin 1 in the clamping arrangement can have the same design as the clamping pin 1 according to the previously described embodiments. However, FIGS. 12 to 15 show a clamping pin 1 having a slightly different design. The clamping pin 1 comprises also a first clamping element 2, a second clamping element 3, a spring 4 and a screw 5. The spring 4 is arranged such that it provides an axial force onto the first clamping element 2 and the second clamping element 3. Thereby it pushes the second clamping element 3 towards the shoulder portion 53 of the screw. It has to be noted that in that embodiment the stationary position is equal or identical to the inserting position.

The first clamping element 2 comprises also an opening 28 that extends along the longitudinal axis of the clamping element 2. The outer section 90 is designed such that it is engageable with the opening 28. In the present embodiment both parts are designed cylindrically and the outer section 90 is being pressed into the opening 28. Other joining techniques, such as a thread, a welded connection etc. can also be used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A clamping pin intended to be inserted into and held in an opening of a medical device, wherein the clamping pin comprising:
    a screw having a longitudinal axis;
    a clamping section being complementary to an opening in a medical device;
    a first clamping element having an inclined surface that is inclined to the longitudinal axis and a first part of the clamping section, and a second clamping element having an inclined surface that is inclined to the longitudinal axis and a second part of the clamping section, wherein the inclined surface of the first clamping element is in contact with the inclined surface of the second clamping element wherein the screw extends at least partly through the second clamping element and at least partly through the first clamping element and wherein the screw engages in one of the clamping elements such that the axial distance between the clamping elements and the diameter of the clamping section that can come in contact with a surface of the opening in the medical device will be changed upon actuation of the screw, wherein the clamping pin further comprises a spring, which is arranged such that it provides an axial force onto one of the clamping elements such that said clamping element is pushed against the other clamping element such that the diameter (D) of the clamping section increases, wherein the increased diameter (D) comes into contact with said surface of the opening in order to provide a spring-biased connection between the medical device and the clamping pin and wherein the diameter (D) can be increased further by actuating said screw in order to provide a clamping force, and wherein the at least one of the clamping elements comprises an element protruding over an outer circumferential surface thereof or into the circumferential surface, wherein said element can be used to move said clamping element against or away from the other clamping element.

2. The clamping pin according to claim 1, wherein the protruding element is capable of moving one clamping element against the spring.

3. The clamping pin according to claim 1, wherein the spring is arranged within a spring room that is provided by an opening in one of the clamping elements.

4. The clamping pin according to claim 1, wherein the first and second clamping elements have substantially the same cross-section in a direction perpendicular to the axis.

5. The clamping pin according to claim 4, wherein the cross-section of said clamping elements is circular, rectangular, quadratic, elliptical or polygonal.

6. The clamping pin according to claim 1, wherein said protruding element is a notch or lug.

7. The clamping pin according to claim 1, wherein two gripping surfaces are arranged angular to each other such that a tool is engageable in order to be rotated.

8. The clamping pin according to claim 1, wherein the at least one of the clamping elements comprises a functional section that is adjacent to the clamping surface, wherein the functional section is a clamping structure to clamp a pin or a rod.

9. The clamping pin according to claim 8, wherein the functional section is a cylinder providing an outer surface onto which the first clamping element is mountable.

10. The clamping pin as set forth in claim 1 wherein the first and second clamping elements having an elongated outer surface and an elongated inner bore, said inner bore and said outer surface defining an inclined wall therebetween having two elongated planar side surfaces, said side surfaces tapering in a radial direction with respect to said longitudinal axis from a first end towards a second end of the inclined wall, a sliding engagement between the first and second clamping elements occurring on facing side surfaces of the first and second clamping elements during movement therebetween in the direction of the longitudinal axis.

11. The clamping pin as set forth in claim 1 wherein the inclined surfaces are planar surfaces and that the clamping section has a circular form as viewed along the longitudinal axis.

12. A clamping pin arrangement comprising two clamping pins intended to be inserted into and held in an opening of a medical device, wherein each clamping pin comprises a screw having a longitudinal axis, a clamping section being complementary to an opening of a medical device;

a first clamping element having an inclined surface that is inclined to the longitudinal axis and a first part of the clamping section, and a second clamping element having an inclined surface that is inclined to the longitudinal axis and a second part of the clamping section, wherein the inclined surface of the first clamping element is in contact with the inclined surface of the second clamping element wherein the screw extends at least partly through the second clamping element and at least partly through the first clamping element and wherein the screw engages in one of the clamping elements such that the axial distance between the clamping pins and the diameter of the clamping section that can come in contact with a surface of the opening in the medical device will be changed upon actuation of the screw, wherein the clamping pin further comprises a spring, which is arrange such that it provides an axial force onto one of the clamping elements such that said clamping element is pushed against the other clamping element such that the diameter (D) of the clamping section increases, wherein the increased diameter (D) comes into contact with said surface of the opening in order to provide a spring-biased connection between the medical device and the clamping pin and wherein the diameter (D) can be increased further by actuating said screw in order to provide a clamping force, and wherein the at least one of the clamping elements comprises an element protruding over an outer circumferential surface or into the circumferential surface, wherein said element can be used to move said clamping element against or away from the other clamping element, wherein said two clamping pins are connected by means of a connection module.

13. The clamping pin as set forth in claim 12 wherein the first and second clamping elements having an elongated outer surface and an elongated inner bore, said inner bore and said outer surface defining an inclined wall therebetween having two elongated planar side surfaces, said side surfaces tapering in a radial direction with respect to said longitudinal axis from a first end towards a second end of the inclined wall, a sliding engagement between the first and second clamping elements occurring on facing side surfaces of the first and second clamping elements during movement therebetween in the direction of the longitudinal axis.

* * * * *